US012266109B2

(12) United States Patent
Newman-Toker et al.

(10) Patent No.: US 12,266,109 B2
(45) Date of Patent: Apr. 1, 2025

(54) PLATFORM TO DETECT PATIENT HEALTH CONDITION BASED ON IMAGES OF PHYSIOLOGICAL ACTIVITY OF A PATIENT

(71) Applicant: The Johns Hopkins University, Baltimore, MD (US)

(72) Inventors: David E. Newman-Toker, Baltimore, MD (US); Jorge Otero-Millan, Baltimore, MD (US); Taylor Maxwell Parker, Winter Park, FL (US); Nathan Farrell, Whitesboro, NY (US)

(73) Assignee: The Johns Hopkins University, Baltimore, MD (US)

( * ) Notice: Subject to any disclaimer, the term of this patent is extended or adjusted under 35 U.S.C. 154(b) by 445 days.

(21) Appl. No.: 17/597,213

(22) PCT Filed: Jul. 23, 2020

(86) PCT No.: PCT/US2020/070304
§ 371 (c)(1),
(2) Date: Dec. 29, 2021

(87) PCT Pub. No.: WO2021/026552
PCT Pub. Date: Feb. 11, 2021

(65) Prior Publication Data
US 2022/0245812 A1 Aug. 4, 2022

Related U.S. Application Data

(60) Provisional application No. 62/883,373, filed on Aug. 6, 2019.

(51) Int. Cl.
*G06K 9/00* (2022.01)
*A61B 5/00* (2006.01)
(Continued)

(52) U.S. Cl.
CPC .......... *G06T 7/0014* (2013.01); *A61B 5/4023* (2013.01); *G06T 7/20* (2013.01);
(Continued)

(58) Field of Classification Search
CPC ...... G06T 7/0014; G16H 40/63; G16H 30/40; G16H 50/20; G16H 15/00; G16H 20/40;
(Continued)

(56) References Cited

U.S. PATENT DOCUMENTS 10,902,602 B1 * 1/2021 Mansi ................... G06T 7/0012
2008/0021731 A1 * 1/2008 Rodgers ............. G08B 21/0469
348/E7.078

(Continued)

FOREIGN PATENT DOCUMENTS

EP 2400934 A1 1/2012

OTHER PUBLICATIONS

International Search Report and Written Opinion issued in International Application No. PCT/US2020/070304; Dated Oct. 22, 2020.

*Primary Examiner* — Alex Kok S Liew
(74) *Attorney, Agent, or Firm* — Harrity & Harrity, LLP

(57) ABSTRACT

A user device may receive video associated with a patient, wherein the video depicts physiological activity involving the patient. The user device may receive profile information associated with the patient. The user device may obtain, from the video, image data using an image processing model. The user device may analyze the image data to generate a patient signature associated with the image data, wherein the patient signature is representative of the physiological activity. The user device may access a reference data structure that includes a plurality of reference signatures. The user device may identify that the patient signature is associated with a reference signature of the plurality of reference signatures, wherein the reference signature is
(Continued)

associated with a health condition. The user device may perform an action associated with the health condition and the patient.

20 Claims, 7 Drawing Sheets

(51) Int. Cl.
*G06T 7/00* (2017.01)
*G06T 7/20* (2017.01)
*G16H 50/30* (2018.01)

(52) U.S. Cl.
CPC ... *G16H 50/30* (2018.01); *G06T 2207/10016* (2013.01); *G06T 2207/30041* (2013.01); *G06T 2207/30201* (2013.01)

(58) Field of Classification Search
CPC ........ G16H 30/20; G16H 50/30; G16H 10/60; G16H 40/20; G16H 50/70; G16H 70/20; G16H 40/67; G16H 20/60; G16H 50/50; G16H 10/40; G16H 20/30; A61B 5/7275; A61B 5/746; A61B 5/7267; A61B 90/361; A61B 1/000096; A61B 2034/252; A61B 2034/256; A61B 34/10; A61B 34/25; A61B 1/04; A61B 1/000094; A61B 17/00; G06V 20/20; G06V 20/52; G06V 40/10; G06V 20/40; G06V 20/41; G06V 20/44; G06V 20/49; G06V 2201/034; G06V 2201/03; G06V 10/25; G06V 10/454; G06V 10/764; G06V 10/82; G06V 40/161; G06V 10/28; G06V 20/64; G06V 20/653; G06V 20/68
See application file for complete search history.

(56) References Cited

U.S. PATENT DOCUMENTS

| | | | |
|---|---|---|---|
| 2009/0210014 A1 | 8/2009 | Ziolo et al. | |
| 2014/0371599 A1* | 12/2014 | Wu | A61B 5/0022 600/476 |
| 2015/0332457 A1* | 11/2015 | Mestha | G06T 7/254 382/103 |
| 2016/0270656 A1* | 9/2016 | Samec | A61B 5/14555 |
| 2018/0001184 A1* | 1/2018 | Tran | G16H 50/20 |
| 2019/0004132 A1 | 1/2019 | Tan et al. | |
| 2019/0083031 A1* | 3/2019 | Hanina | A61B 5/1128 |
| 2020/0312455 A1* | 10/2020 | Bhalotia | G16H 20/60 |
| 2021/0045679 A1* | 2/2021 | Finkel | G16H 50/20 |
| 2021/0312183 A1* | 10/2021 | Bendre | G06V 10/764 |
| 2022/0101655 A1* | 3/2022 | Chan | A61B 5/165 |
| 2023/0162851 A1* | 5/2023 | Family | G16H 40/67 705/2 |

* cited by examiner ation PCT/US2020/070304 filed on Jul. 23, 2020,
PLATFORM TO DETECT PATIENT HEALTH CONDITION BASED ON IMAGES OF PHYSIOLOGICAL ACTIVITY OF A PATIENT

CROSS-REFERENCE TO RELATED APPLICATIONS

This Patent Application is a 371 national stage of PCT Application PCT/US2020/070304 filed on Jul. 23, 2020, entitled "PLATFORM TO DETECT PATIENT HEALTH CONDITION BASED ON IMAGES OF PHYSIOLOGICAL ACTIVITY OF A PATIENT," which claims priority to U.S. Provisional Patent Application No. 62/883,373, filed on Aug. 6, 2019, and entitled "PLATFORM TO DETECT PATIENT HEALTH CONDITION BASED ON IMAGES OF PHYSIOLOGICAL ACTIVITY OF A PATIENT," both of which are hereby expressly incorporated by reference herein.

BACKGROUND

Vertigo and dizziness are sensations that may be experienced by patients. Vertigo is the false sensation of self-motion when no self-motion is occurring or the sensation of distorted self-motion during an otherwise normal head movement. Dizziness is the sensation of disturbed or impaired spatial orientation without a false or distorted sense of motion. Vertigo or dizziness or other similar balance-related symptoms (referred to herein as "vertigo") can be caused by an inner ear impairment or other type of disease. In some instances, vertigo is a sign that a patient is about to have or is having a stroke or other type of disease.

SUMMARY

According to some implementations, a method may include receiving video associated with a patient, wherein the video depicts physiological activity involving the patient; receiving profile information associated with the patient, wherein the profile information identifies profile characteristics of the patient; obtain, from the video, image data using an image processing model, wherein the image processing model is configured to obtain images associated with the physiological activity, wherein the physiological activity involves an eye of the patient or a head of the patient, and wherein the image data corresponds to the images; analyzing the image data to generate a patient signature associated with the image data, wherein the patient signature is representative of the physiological activity; accessing a reference data structure that includes a plurality of reference signatures corresponding to the physiological activity, wherein the plurality of reference signatures are associated with at least one of the profile characteristics; identifying that the patient signature is associated with a reference signature of the plurality of reference signatures, wherein the reference signature is associated with a health condition; and performing an action associated with the health condition and the patient.

According to some implementations, a user device may include one or more memories and one or more processors, communicatively coupled to the one or more memories, to: receive profile information associated with a patient, wherein the profile information identifies profile characteristics of the patient; cause a camera to capture video of the patient; process, using a first model, the video to obtain first image data associated with eye movement of the patient; process, using a second model, the video to obtain second image data associated with head movement of the patient; generate, according to a signature model, a patient signature associated with the first image data, the second image data, and the profile information; determine that the patient signature matches a reference signature in a reference data structure, wherein the reference signature is associated with the signature model, and wherein the reference signature is mapped, in the reference data structure, with information identifying a health condition; and perform an action associated with indicating that the patient has the health condition.

According to some implementations, a non-transitory computer-readable medium may store one or more instructions. The one or more instructions, when executed by one or more processors of a user device, may cause the one or more processors to: receive, via a user interface, profile information associated with a patient, wherein the profile information identifies profile characteristics of the patient; cause, based on a user input received via the user interface, a camera to capture video of the patient; obtain, from the video and using a facial analysis model, image data associated with one or more physiological characteristics of the patient; generate, according to a signature model, a patient signature associated with the image data and the profile information; compare the patient signature to a plurality of reference signatures in a reference data structure, wherein the plurality of reference signatures are generated using the signature model; determine, based on a portion of the patient signature matching a threshold portion of a reference signature of the plurality of reference signatures, whether the patient has a particular health condition, wherein the reference signature is mapped, in the reference data structure, with information identifying the health condition; and perform, based on whether the patient has the health condition, an action associated with the patient.

DETAILED DESCRIPTION

Figure 1:
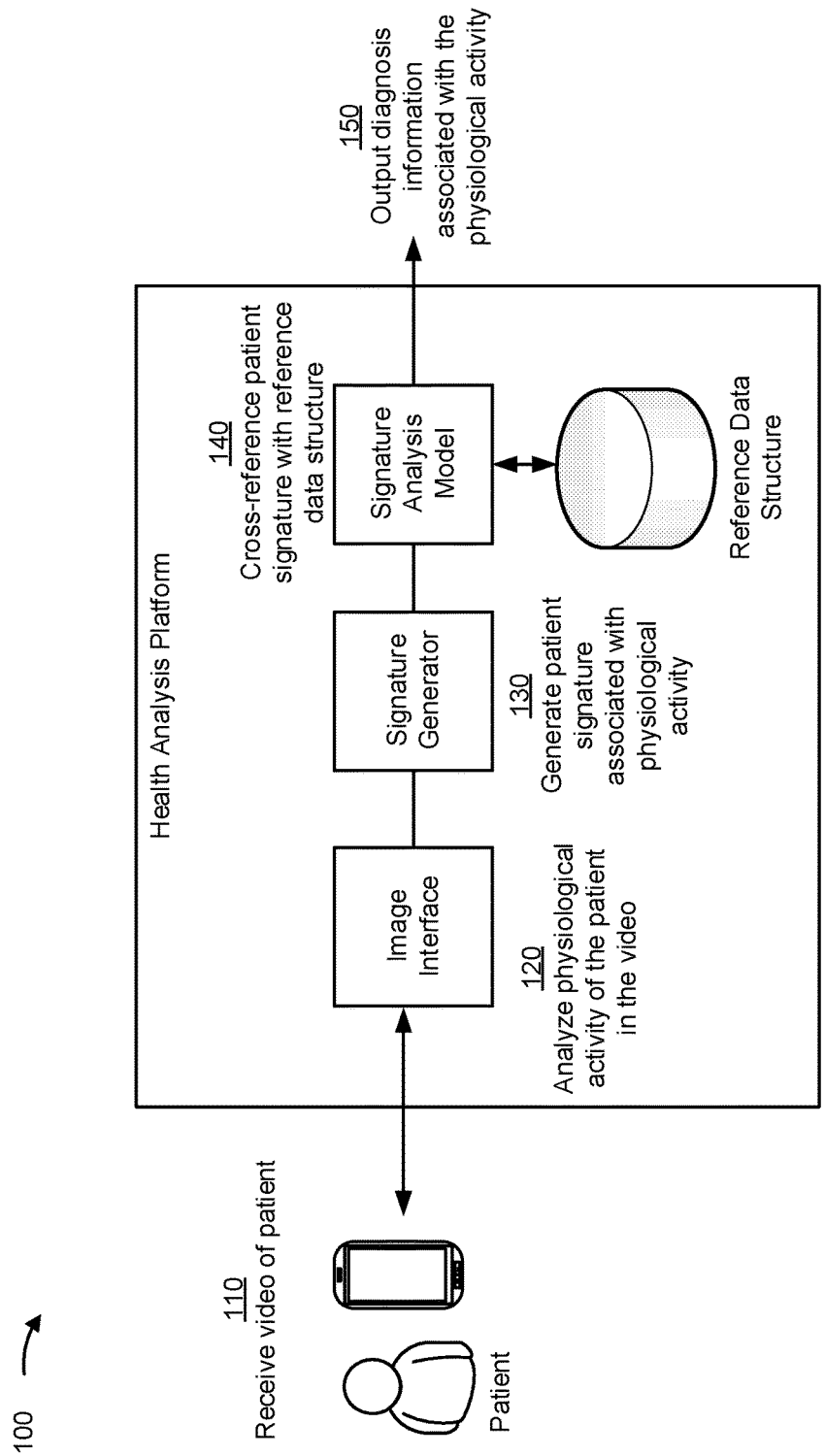
FIGS. 1 and 2 are diagrams of an example implementation described herein.

The following detailed description of example implementations refers to the accompanying drawings. The same reference numbers in different drawings may identify the same or similar elements.

In some instances, a patient that is experiencing vertigo (or dizziness) may have a relatively benign inner ear impairment or disease (e.g., benign paroxysmal positional vertigo (BPPV)). In such cases, the patient likely does not need to receive urgent medical care and/or may potentially be treated remotely (e.g., via instructions for self-administered treatment). On the other hand, in some instances, vertigo can be a sign that the patient is experiencing a stroke (or may soon experience a stroke). In such cases, the patient should receive medical care to prevent such a stroke from causing severe damage to the health of the patient (e.g., brain damage) or death. In some instances, patterns associated with eye movement, changes to facial features, head movement, and/or other bodily movement (e.g., patterns of walking (e.g., gait), standing, being at rest, exercising, and/or other types of human activity) may be signs of whether the patient has an inner ear impairment or the patient is experiencing a stroke.

Previous techniques to analyze eye movement, changes to facial features, head movement, and/or other bodily movement of a user involve using a dedicated monitoring device that uses a complex system of sensors (e.g., a device that is mounted to a patient's head to measure eye and head movement, a device laid out beneath the patient to measure bodily movement, such as the patient's gait, balance, or exercise ability, and/or the like). For example, a monitoring device mounted to a patient's head may assist a medical professional (e.g., a physician, a nurse, and/or the like) in performing a Head Impulse, Nystagmus, and Test of Skew (HINTS) examination. The HINTS examination may permit the physician to determine whether the patient is experiencing a stroke or the patient has an inner ear impairment. However, such monitoring devices are typically owned and/or operated in healthcare facilities (e.g., hospitals, doctor offices, and/or the like), and thus are not readily available to a patient and/or may not be accessible to a patient that is not at such a healthcare facility. Such limited access may prevent a patient from being able to use the monitoring devices in a timely manner, resulting in potentially catastrophic results (e.g., brain damage, death, and/or the like). Moreover, such a complex system of sensors, which may include accelerometers, gyroscopes, cameras, and/or the like, may require specialized assembly to configure the monitoring device to analyze physiological activity of a patient that is experiencing vertigo which incur relatively high costs.

According to some implementations described herein, a health analysis platform may utilize video of physiological activity (e.g., eye movement, head movement, and/or other bodily movement) associated with a patient (e.g., during a particular event or during certain activity) to determine whether the patient is associated with or experiencing a particular health condition. According to some implementations, the video (which may include a series or stream of images) may be captured and provided by a camera of a user device. The health analysis platform may be included within and/or communicatively coupled with the user device to permit the user device to determine (or determine a likelihood of), in real-time, whether a patient experiencing vertigo is experiencing a stroke, has an inner ear impairment, and/or any other type of health condition that may be associated with vertigo. In some implementations, the health analysis platform may be accessed and/or utilized via an application running on the user device. The health analysis platform may determine whether the patient has or is about to have a particular health condition (e.g., is experiencing a stroke, has an inner ear impairment, and/or the like) based on an analysis of eye movement captured in the video, an analysis of facial features captured in the video, an analysis of head movement or other bodily movement captured in the video, profile information associated with the patient, and/or the like. In some implementations, the health analysis platform may generate patient signatures associated with the eye movement, the head movement, the body movement, and/or the profile information and compare the patient signature to one or more reference signatures associated with one or more health conditions to determine whether the patient has one or more of the one or more health conditions.

In this way, the health analysis platform enables a user device, which may include a camera or be communicatively coupled to a camera, to be used to detect whether a patient has a particular health condition based on video of physiological activity of the patient. An application associated with the health analysis platform may be installed on a user device (e.g., a smartphone, a computer, and/or the like) that is readily available to the patient and/or a representative of the patient. In this way, relative to previous techniques, a less complex, less expensive, and more readily available system is available to patients to permit the patients to more quickly determine whether the patient requires urgent medical care. Furthermore, the health analysis platform described herein may indicate that a patient likely does not require urgent medical care, which may thus prevent unnecessary and/or frivolous requests from medical personnel (e.g., emergency medical technicians (EMTs), nurses, doctors) to treat the patient, which enables such medical personnel to be more available to those patients that do require urgent medical care. Accordingly, not only can the health analysis platform, described herein, more quickly and efficiently identify potential emergency situations involving a patient, and correspondingly help preserve the health of the patient, the health analysis platform may also assist in preserving the health of other patients that require such emergency personnel that might otherwise be attending to a patient in a non-emergency situation (e.g., a patient experiencing vertigo due to an inner ear impairment).

As described herein, one or more artificial intelligence techniques, including machine learning, deep learning, neural networks, and/or the like can be used to identify, from image data, physiological activity of a patient (e.g., physiological activity associated with an eye, head, or other body parts (e.g., arms, legs, and/or the like) of the patient), determine, from the image data, movement (or lack of movement) of one or more body parts (e.g., eyes, head, arms, legs, and/or the like) of the patient, identify patterns associated with the movement, generate a signature associated with the movement, determine whether the patient signature matches a reference signature associated with a particular health condition, and/or the like. For example, the health analysis platform may use a computer vision technique, such as a convolutional neural network technique to assist in classifying image data (e.g., image data including representations of eyes of a patient, of a head of the patient, a skeletal structure of the patient, and/or the like) into a particular class. More specifically, the health analysis platform may determine that a patient's eye has a particular characteristic (e.g., gaze direction, iris/pupil dilation, movement pattern, and/or the like), the patient's head has a particular characteristic (e.g., is facing a particular direction (e.g., relative to the patient's torso, relative to the patient's gaze direction, and/or the like)), or the patient's body (e.g., skeletal structure) has a particular characteristic (e.g., is positioned in a particular manner). On the other hand, the health analysis platform may determine that the patient's eyes do not have a particular characteristic, that the patient's head does not have a particular characteristic, or that the patient's body does not have a particular characteristic. In implementations cases, the computer vision technique may include using an image recognition technique (e.g., an Inception framework, a ResNet framework, a Visual Geometry Group (VGG) framework, and/or the like), an object detection technique (e.g. a Single Shot Detector (SSD) framework, a You Only Look Once (YOLO) framework, and/or the like), an edge detection technique, an object in motion technique (e.g., an optical flow framework and/or the like), and/or the like. Additionally, or alternatively, the computer vision technique may include an image processing technique configure to analyze particular biometrics of an individual (or patient). For example, the computer vision technique may include a gaze detection technique (e.g., based on an eye detection technique, an iris detection technique, a pupil detection technique, and/or the like), a facial recognition technique, a gait detection technique, and/or the like.

As used herein, when discussing the "eyes" of a patient, similar analyses or methods may be individually and/or separately performed on each eye of the patient or only on one eye of the patient. Although some implementations described herein may be described in connection with diagnosing stroke and/or inner ear impairment, one or more of the processes described herein may similarly be utilized to diagnose any other suitable health condition, such as low blood pressure, abnormal heart rhythm, a concussion, multiple sclerosis, encephalitis, Parkinson's disease, Wernicke's syndrome, and/or the like.

FIG. 1 is a diagram of an example implementation 100 described herein. Example implementation 100 includes a user device and a health analysis platform. The health analysis platform may include an image interface, a signature generator, a signature analysis model, and a reference data structure. As described herein, the user device provides information associated with a patient (e.g., an individual or a user associated with the user device) and/or a video to the health analysis platform to permit the health analysis platform to determine whether the user has a particular medical condition. For example, the health analysis platform may determine whether the video indicates, from physiological activity captured in the video, that the patient is experiencing a stroke or has an inner ear impairment. The health analysis platform may be included within and/or separate from the user device. According to some implementations, an application (e.g., a health analysis application) may be installed on the user device to permit the user device to interact with the health analysis platform.

As shown in FIG. 1 and by reference number 110, the health analysis platform receives video of the patient. The health analysis platform may receive (e.g., in real-time) the video as a stream of images (e.g., frames of video) to permit the health analysis platform to analyze the video, as described herein, while the video is being streamed to the health analysis platform. For example, the user device may include a camera (or other type of image capture device) that is capable of capturing, recording, and/or providing the video, which may correspond to a stream or sequence of images (e.g., frames of the video). In some implementations, the camera may be capable of capturing images that satisfy a threshold resolution (e.g., corresponding to a standard, a regulation, and/or the like). The camera and/or the user device may stream (e.g., in real-time) the captured video to a user interface (e.g., a display) of the user device and/or a user interface of the health analysis platform (e.g., that may be monitored or viewed by a medical professional). Additionally, or alternatively, the images and/or video may be stored as a whole or complete media file and provided (within one or more data communications) to the health analysis platform. As described herein, the video may depict physiological activity of the patient, such as physiological activity associated with the patient's eyes, face, head, limbs, and/or the like. For example, the physiological activity may correspond to one or more changes (or lack of any change) to features of the patient's eyes (e.g., eye movement, pupil dilation, gaze direction, and/or the like), one or more changes to features of the patient's face (e.g., changes to facial expression, changes mouth shape, changes eye brow position, and/or the like), changes to head position and/or orientation, body position and/or orientation, and/or the like.

According to some implementations, the health analysis platform may receive profile information associated with the patient. For example, the patient (e.g., when installing and/or registering with a health analysis application on the user device) may provide information associated with the patient. Such information may include one or more profile characteristics of the patient, such as a name, a residence address, medical symptoms, a past medical history, prescribed medications, a date of birth (or age), a height, a weight, a sex, a race, and/or the like.

In some implementations the profile information may include symptom information associated with the patient. For example, the symptom information may include details of one or more symptoms experienced by the patient. The symptom information may include information identifying a type of symptom (e.g., dizziness, weakness, shortness of breath, pain, location of pain, and/or the like), duration of a symptom (e.g., an hour, 5 hours, a day, and/or the like), an intensity of a symptom, triggers of a symptom (e.g., change in head position), and/or the like. Accordingly, the profile information may indicate symptoms experienced by the patient.

Additionally, or alternatively, the profile information may include sign information that is observable or measurable (e.g., slow heart rate, abnormal eye movements, motor paralysis, and/or the like). For example, the sign information may include details of one or more signs observed by an individual (e.g., a user of the user device, if not the patient, a representative of the patient, and/or the like). Additionally, or alternatively, the sign information may include sensor information corresponding to measurements from sensors of the user device. For example, an accelerometer, gyroscope, temperature sensor, microphone, and/or the like may be used to obtain measurements associated with the patient when the patient is holding or personally utilizing a phone to record the video. The measurements may indicate characteristics of the patient's balance, may measure a gait of the patient, may indicate whether the patient is having tremors, may indicate whether the patient has a fever, and/or the like.

In some implementations, a health analysis application of the user device may prompt a user (e.g., the patient or a representative of the patient) for the profile information. For example, if the profile information has not been obtained already, the health analysis application may cause a user interface to prompt the user for the profile information upon capturing the video and/or providing the video to the health analysis platform. Additionally, or alternatively, the health analysis platform may request the profile information upon receipt of the video (which may cause the health analysis application to prompt the user for the information). In some implementations, the health analysis platform may prompt the user device to capture measurements from sensors of the user device to permit the measurements to be included in the profile information. In some implementations, the health analysis platform may cause the user to device to prompt the patient to hold the user device in a particular manner or request the patient to attempt to perform one or more activities (e.g., walk, balance on one foot, wink, and/or the like).

In this way, the health analysis platform may receive profile information that is specific to the patient. Accordingly, such profile information may be linked to the images and/or video to permit the health analysis platform to analyze the physiological activity of the patient in view of or in combination with the profile information, as described herein.

The camera (and/or, correspondingly, the user device) may be positioned to capture physiological activity of the user. Such physiological activity may be specific to one or more parts of the patient's body. For example, the camera may be positioned to capture video of the user's eyes, face, head, body, and/or the like. In some implementations, the user device, via a user interface, may display instructions and/or a frame in which the patient's eyes, face, head, or other body parts are to be positioned within the field of view of the camera (e.g., to enable optimal video, according to one or more models described herein, of the desired physiological activity to be captured).

The patient may be any individual or subject that may have a health condition or that is experiencing a medical emergency (or signs of a potential medical emergency). For example, the patient may be an individual that is experiencing vertigo, showing signs of vertigo or dizziness (e.g., uncontrolled or rapid eye movement, head movement, body movement, and/or the like), and/or the like. Accordingly, the patient may be a potential stroke patient and/or a patient with an inner ear impairment. In some implementations, the patient is associated with or is a user of the user device (e.g., the patient may be registered to the user device, has an account associated with the user device or a health analysis application of the user device, and/or the like).

In this way, the health analysis platform may receive video that depicts physiological activity of the patient to permit the health analysis platform to determine whether the patient has a particular health condition (e.g., a health condition that may or may not require immediate or urgent medical care).

As further shown in FIG. 1, and by reference number 120, the health analysis platform analyzes physiological activity of the patient in the images and/or the video. For example, the health analysis platform may process the video (and/or image data if preprocessed by the user device) to enable physiological activity associated with the patient to be analyzed. For example, the image interface may receive the video and process the video using one or more models (e.g., a gaze detection model, a facial recognition model, and/or the like).

According to some implementations, the health analysis platform (e.g., if receiving unprocessed view from the user device) may utilize one or more image processing models to extract image data associated with specific physiological activity. For example, the health analysis platform, using a first image processing model (e.g., a gaze detection model, an iris detection model, and/or the like), may extract image data from the video that corresponds to images of the eyes of the patient. Additionally, or alternatively, the health analysis platform, using a second image processing model (e.g., a facial recognition model, a human detection model, and/or the like) may extract image date from the video that corresponds to images of the head of the patient. In some implementations, the health analysis platform, using a third image processing model (e.g., a gait detection model, a gait analysis model, and/or the like) may extract image data from the video that corresponds to images of the body or skeletal structure of the patient. In such cases, the health analysis platform may process the video to remove image data (e.g., by cropping selective portions of the images) that may not be needed for one or more processes described herein. In this way, the health analysis platform may conserve computing resources that may otherwise be immaterial relative to one or more processes described herein, and/or network resources associated with communicating image data that may be immaterial to one or more processes described herein.

Such image processing models may be configured to identify particular features and/or locations (e.g., coordinates of the frame of the video, coordinates relative to one or more reference points in the frames in the video, and/or the like) of one or more body parts of the patient. For example, the image processing model may determine, in each frame of video, a position of the patient's eyes (e.g., relative to the patient's eye sockets or head), and/or eye movement of the patient's eyes, such as movement of the pupil within an eye of the patient, dilation or constriction (which may be referred to herein simply as "dilation") of the pupil and/or iris (e.g., corresponding to the size of the pupil and/or speed of iris movement), a position or change of position of the patient's eyelids (e.g., which may be representative of how open the patient's eyelids are), and/or the like. Additionally, or alternatively, an image processing model may determine, for each frame of video, a position of the patient's head (e.g., relative to the patient's torso). Additionally, or alternatively, an image processing model may determine, for each frame of video, a position of the patient's limbs (e.g., relative to the patient's torso, and/or other limbs). From such an analysis, the image processing model may store physiological activity information that corresponds to the physiological activity depicted in the video. Accordingly, using the physiological activity information for each frame of the video, the health analysis platform may determine movement associated with the eyes of the patient (referred to herein as "eye movement"), movement associated with the head of the patient (referred to herein as "head movement"), and/or movement associated with the body or skeletal structure of the patient (referred to herein as "body movement"). More specifically, based on changes in coordinates of one or more features of the eyes, head of the patient, or body of the patient the health analysis platform may determine a path and/or pattern of movement of the patient's eyes, head, or body. Accordingly, the health analysis platform may analyze, in the depicted physiological activity, the movement of an eye of the patient, the dilation of an eye of the patient, the position of an eye of the patient, the movement of a head of the patient, the position of a head of the patient, a gait of the patient, a balance capability of the patient (e.g., during a certain activity), and/or the like.

According to some implementations, the health analysis platform may receive the above corresponding image data from the user device. For example, the user device may be similarly capable of processing the video to extract desired image data in accordance with one or more processes described herein.

In this way, the health analysis platform may determine analyze the physiological activity to determine one or more characteristics (e.g., eye movement, head movement, body movement, and/or the like) of the physiological activity to permit the health analysis platform to generate a signature associated with the physiological activity.

As further shown in FIG. 1, and by reference number 130, the health analysis platform may generate a patient signature associated with the physiological activity. The patient signature may be a digital representation of the physiological activity.

In some implementations, the health analysis platform may use a signature model (e.g., a mapping model, a mapping scheme, and/or the like) to generate a patient signature associated the physiological activity. Such a signature model may correspond to a signature model used to generate reference signatures stored in the reference data structure.

According to some implementations, the patient signature is generated based on translating, according to a signature model, physiological activity information to data points (or data values) of the signature. For example, the health analysis platform may translate coordinates of eye movement (e.g., coordinates associated with a location or reference points of an iris or pupil of an eye within an image (referred to herein as "image coordinates")) and/or coordinates of head movement (e.g., image coordinates associated with a location or reference point of a facial feature (a nose, eyes, ears, mouth, lips, and/or the like) of the patient), and/or coordinates of body movement (e.g., image coordinates associated with a location or reference point of a skeletal feature (e.g., a limb, a joint of a limb, a torso, a neck, the head, and/or the like) to data points to generate the patient signature. The data points may be combined to form the patient signature.

In some implementations, the data points may be combined with profile information. For example, the profile information can be translated into profile data points of the signature. The profile data points may be appended to and/or added to the data points generated from the physiological activity information to generate the patient signature. Additionally, or alternatively, the profile data points may be used as one or more weights (e.g., based on values of certain profile characteristics of the profile information) to skew or alter the data points determined from the physiological activity information.

In this way, the health analysis platform may generate a patient signature corresponding to one or more characteristics of the physiological activity to permit the health analysis platform to determine whether the patient has a particular health condition associated with a reference signature in the reference data structure.

As further shown in FIG. 1, and by reference number 140, the health analysis platform may cross-reference the patient signature with the reference data structure. For example, the signature analysis model may perform a lookup operation to determine whether the patient signature matches (e.g., according to a threshold match, according to one or more matching analyses, such as heuristic matching, probabilistic matching, iterative matching, machine learning, and/or the like) one or more reference signatures in reference data structure. The reference signatures of the reference data structure may be generated in accordance with a same signature model used to generate the patient signature. The reference data structure may be any suitable data structure, such as a table, an index, a list, a graph, and/or the like.

The reference data structure may include a plurality of reference signatures. Each of the reference signatures may be representative of physiological activity (e.g., eye movement, changes to facial features, head movement, body movement, and/or the like) that is a sign of a corresponding health condition. For example, the plurality of reference signatures may be representative of physiological activity associated with vertigo. Accordingly, some of the reference signatures may be representative of physiological activity that is indicative of or known to be a sign of stroke, and other reference signatures may be representative of physiological activity that is indicative of or known to be a sign of inner ear impairment low blood pressure, abnormal heart rhythm, and/or other disease.

In some implementations, each of the reference signatures are associated with historical physiological activity associated with other patients (e.g., other patients that previously experienced vertigo). For example, the reference signature may be generated from physiological activity of a patient that is known to have a particular health condition. Additionally, or alternatively, the reference signature may be generated by processing (e.g., combining, averaging, summing, and/or the like) reference signatures from a plurality of patients (e.g., patients with same profile characteristics) known to have a particular health condition. Furthermore, each of the reference signatures is mapped to a corresponding health condition that is represented by the reference signature. In this way, as described herein, if the patient signature matches one or more of the reference signatures (e.g., according to a threshold match and/or matching analysis), the health analysis platform may determine that the patient has the health condition mapped to the one or more reference signatures.

In some implementations, the reference data structure includes reference signatures that were generated from and/or associated with patients that have one or more of the same profile characteristics (as identified in the profile information) as the patient. For example, the reference data structure may be one of a plurality of reference data structures that are sorted and/or organized according to profile characteristics of patients that were monitored and/or analyzed is association with generating the reference signatures. In some implementations, the reference data structure may be organized and/or sorted by one or more profile characteristics. In such a case, the health analysis platform may only analyze or compare the patient signature to the reference signatures generated from analyzing patients have one or more of the same or similar profile characteristics as the patient. Therefore, because such profile characteristics may affect the physiological activity analyzed by the health analysis platform, the health analysis platform may achieve improved accuracy with respect to determining whether the patient has a particular health condition. Furthermore, comparing only the reference signatures that are mapped to the same profile characteristics, the health analysis platform may conserve computing resources that may otherwise be used analyzing reference signatures associated with patients that have different profile characteristics than the patient and/or that may be ineffective in determining whether the patient has a particular health condition, as described herein.

In some implementations, the reference data structure is configured to store training data associated with a machine learning model configured to analyze physiological activity associated with a patient and to make and/or indicate a diagnosis based on the physiological activity. In such cases, the health analysis platform may use such a machine learning model, such as a health analysis model, to determine whether the patient has a particular health condition, to determine a probability that the patient has a particular condition, and/or to diagnose the patient with a particular health condition. For example, the health analysis platform may train the health analysis model based on one or more diagnosis parameters associated with images or video of physiological activity of a plurality of patients, such as eye movement, dilation, eye position, eyelid position, head movement, body movement, head position, facial feature position, changes to facial features, characteristics of facial features (e.g., color, which may indicate temperature or heart rate), profile characteristics, symptom information, sign information, and/or the like. The health analysis platform may train the health analysis model using historical data associated with diagnosing the health condition (or other health conditions) according to the one or more diagnosis parameters. Such historical data may be based on or include feedback (e.g., based on user inputs from medical professionals that confirm or deny an accuracy of the diagnosis). Using the historical data and the one or more diagnosis parameters as inputs to the health analysis model, the health analysis platform may determine whether the physiological activity is indicative of a particular health condition to indicate whether a subject patient has that health condition. Accordingly, in some implementations, the health analysis platform may store the generated patient signature in the reference data structure to further train such a health analysis model.

To determine whether the patient has a particular health condition (e.g., a health condition mapped to one or more of the reference signatures), the health analysis platform determines whether the patient signature matches one or more of the reference signatures. For example, the health analysis platform may compare the patient signature to one or more reference signatures (e.g., one or more reference signatures that are associated with patients having a same trait as the patient) and determine whether the patient signatures matches any of the one or more reference signatures.

In some implementations, the health analysis platform determines that the patient signature matches the reference signature when a threshold portion (e.g., a threshold percentage (e.g., 70%, 85%, 90%, and/or the like), a threshold number of a set of particular data points, and/or the like) of data points of the patient signature match corresponding data points of the reference signature. As a specific example, if the signatures are sequences of 10 data points and the threshold is 70% for a match, if 7 or more of the data points of the patient signature match corresponding data points (in the sequence) of the reference signature, the health analysis platform may determine that the patient signature matches the reference signature. On the other hand, if less than 7 of the data points of the patient signature match corresponding data points (in the sequence) of the reference signature, the health analysis platform may determine that the patient does not match the reference signature. In another example, if a particular portion of the patient signature is a match (or a threshold match) of a corresponding portion of a reference signature that is mapped as being indicative of a particular health condition, the health analysis platform may determine that the patient has the particular health condition (regardless of how much of the remaining patient signature matches the remaining reference signature).

According to some implementations, the health analysis platform may determine a probability that the patient has a particular condition based on a measure of similarity between the patient signature and one or more of the reference signatures. For example, the more accurately that a patient signature matches a reference signature, the greater the probability that the patient has the health condition associated with that reference signature (and vice versa). Additionally, or alternatively, the greater the quantity of reference signatures associated with a particular health condition that match the patient signature, the greater the probability that the patient has that health condition.

In some implementations, the health analysis platform may determine respective probabilities of the patient having any of the health conditions represented by the reference signatures in the reference data structure. For example, assume that the reference data structure includes a first plurality of reference signatures associated with patients having a stroke and a second plurality of reference signatures associated with patients having an inner ear impairment. In such an example, the health analysis platform may determine, based on how accurately the patient signature matches each of the reference signatures in the reference signature database (or each of a subgroup of the reference signatures in the reference signature database), the probability that the patient is having a stroke and the probability that the patient has an inner ear impairment. Accordingly, if the physiological activity indicates that the patient is experiencing vertigo (or if the health analysis platform receives an indication that the patient is experiencing vertigo), the health analysis platform may determine that the patient may be having a stroke or may have an inner ear impairment, and correspondingly determine the respective probabilities that the patient has those health conditions.

In this way, the health analysis platform may cross-reference the patient signature with a reference data structure to determine whether the patient signature matches one or more of the reference signatures to permit the health analysis platform to determine whether the patient has (or has a probability of having) a particular health condition.

As further shown in FIG. 1, and by reference number 150, the health analysis platform may output diagnosis information associated with the physiological activity. For example, the health analysis platform may output a diagnosis that indicates whether the patient has a particular health condition based on the whether the patient signature matched one or more of the reference signatures in the reference data structure. If the patient signature matches one or more reference signatures (e.g., or a threshold quantity or percent of reference signatures associated with the particular health condition), the health analysis platform may indicate that the patient has (or likely has, according to a particular probability) a corresponding health condition. In some implementations, the diagnosis information may include information identifying a determined probability that the patient has a particular health condition.

In some implementations, the health analysis platform may provide the diagnosis information via a user interface. For example, the health analysis platform may cause a display of the user device (and/or one or more other user devices communicatively coupled with the health analysis platform) to present whether the patient has the health condition, a treatment plan associated with the health condition, contact information associated with a healthcare provider that can treat the health condition, whether urgent medical attention should be given to the patient, and/or the like.

As described herein, the health condition may require urgent attention to conserve the health (or life) of the patient and/or may not require urgent attention to conserve the health (or life) of the patient. In some implementations, if the health analysis platform determines that the patient likely has a health condition that requires urgent medical attention, the health analysis platform may notify one or more entities (e.g., an emergency response entity, a medical professional, an alert system of a medical facility, and/or the like).

In some implementations, based on whether the health analysis platform determines that the patient has a particular health condition, the health analysis platform may transmit a communication that includes the diagnosis information. Additionally, or alternatively, the communication may include profile information of the patient, location information of the patient (e.g., as determined from a geolocation system of the user device), and/or the like. In this way, the health analysis platform may notify to notify an entity (e.g., a healthcare provider, such as a medical professional, an emergency response entity, and/or the like).

In this way, the health analysis platform may perform one or more actions associated with indicating whether the patient has a particular health condition to permit the patient to receive appropriate and/or requisite health care.

As indicated above, FIG. 1 is provided merely as one or more examples. Other examples may differ from what is described with regard to FIG. 1.

Figure 2:
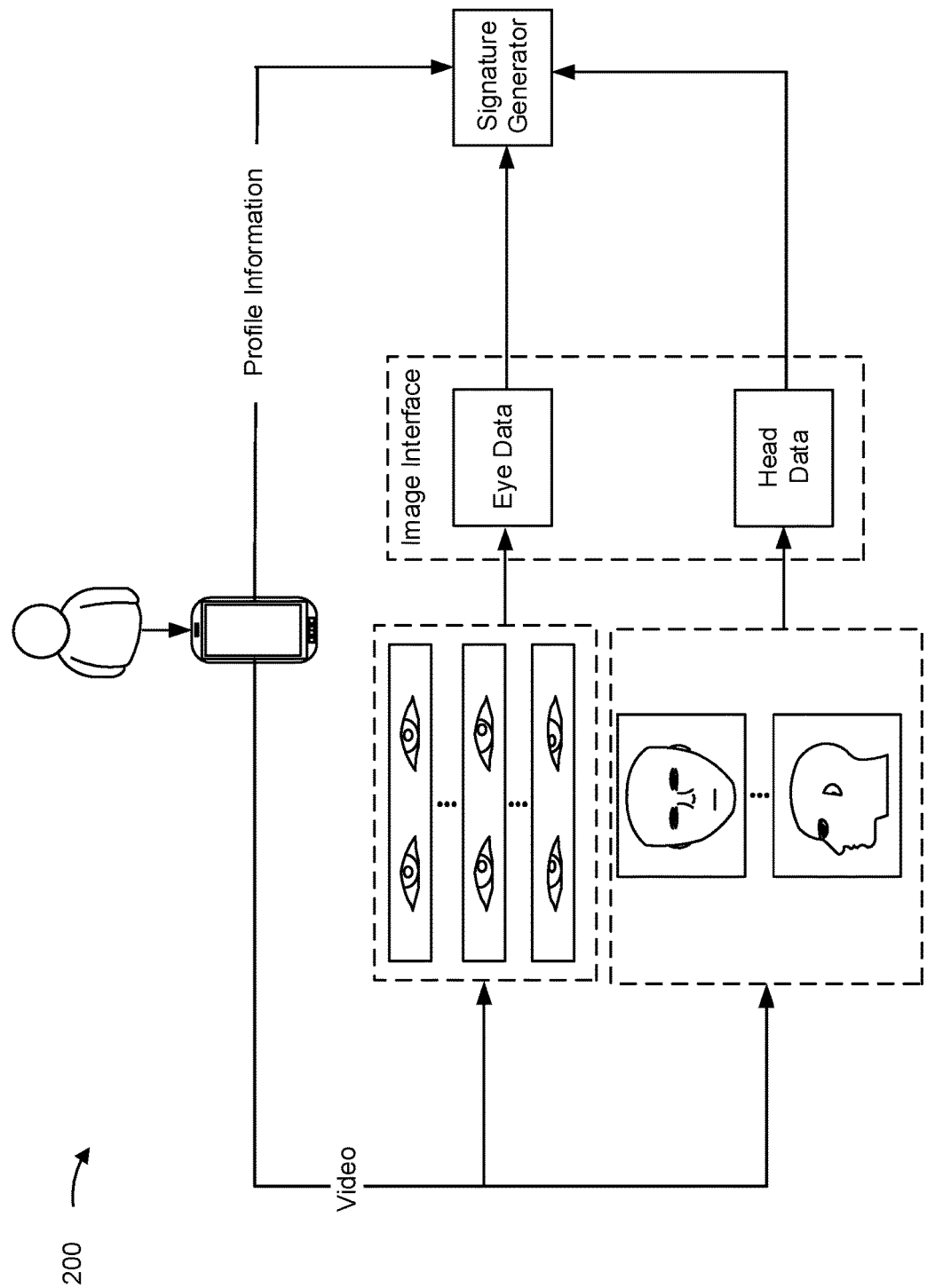

FIG. 2 is a diagram of an example implementation 200 described herein. Example 200 includes an example of implementation of data and/or information that may be used by the signature generator to generate a signature. As described herein, the signature generator may generate a patient signature according to a signature model. In FIG. 2, the signature model may utilize profile information, eye data, and head data to generate a signature. In some implementations, the signature model of example implementation may also utilize body (or skeletal) data to generate the signature (e.g., based on an analyzed gait or other movement of a patient).

As shown in FIG. 2, the user device provides profile information and video. The video includes frames with images of eyes and images of a patient's head. In some implementations, the images of the eyes and the head were preprocessed (e.g., extracted) from the video captured by the user device. As shown, in different frames of the video, the eyes may be in different positions (e.g., be looking in different directions or have different gaze directions), have a different dilation, and/or have different openness. The image interface may generate corresponding eye data (e.g., representative of the position, dilation, and openness of the eyes) for each of the frames of the image data associated with the patient's eyes. Furthermore, as shown, in different frames of the video, the head may be in different positions (e.g., be facing different lateral directions, have different tilts, and/or the like), perhaps due to shaking laterally. Correspondingly, the image interface may generate head data for each of the frames of the image data associated with the head.

As described herein, from the eye data, the signature generator may convert (or translate) coordinates of features (e.g., iris, pupil, gaze direction, position, openness, and/or the like) of one of more eyes of the patient to generate eye data points of the patient signature. Further, from the head data, the signature generator may convert coordinates of features (e.g., mouth, nose, lips, eyes, face, and/or the like) of the patient to generate head data points of the patient signature. The signature generator may then combine the eye data points and the head data points with the profile information using any suitable technique (e.g., summation, averaging, weighting, and/or the like). According to some implementations, the signature generator may use a hash function to generate the patient signature based on the eye data, the head data, and/or the profile information.

As indicated above, FIG. 2 are provided merely as one or more examples. Other examples may differ from what is described with regard to FIG. 2.

Accordingly, as described herein, the health analysis platform may utilize video and/or image data, captured by a user device, to determine whether a patient has a particular health condition. Such a user device, video, and/or image may be more accessible to patients that may have a particular medical condition (relative to previous techniques), and thus may allow for a more quick and efficient determination of whether the patient has a particular health condition, which can prove beneficial in preserving the health and/or life of the patient or other patients.

Figure 3:
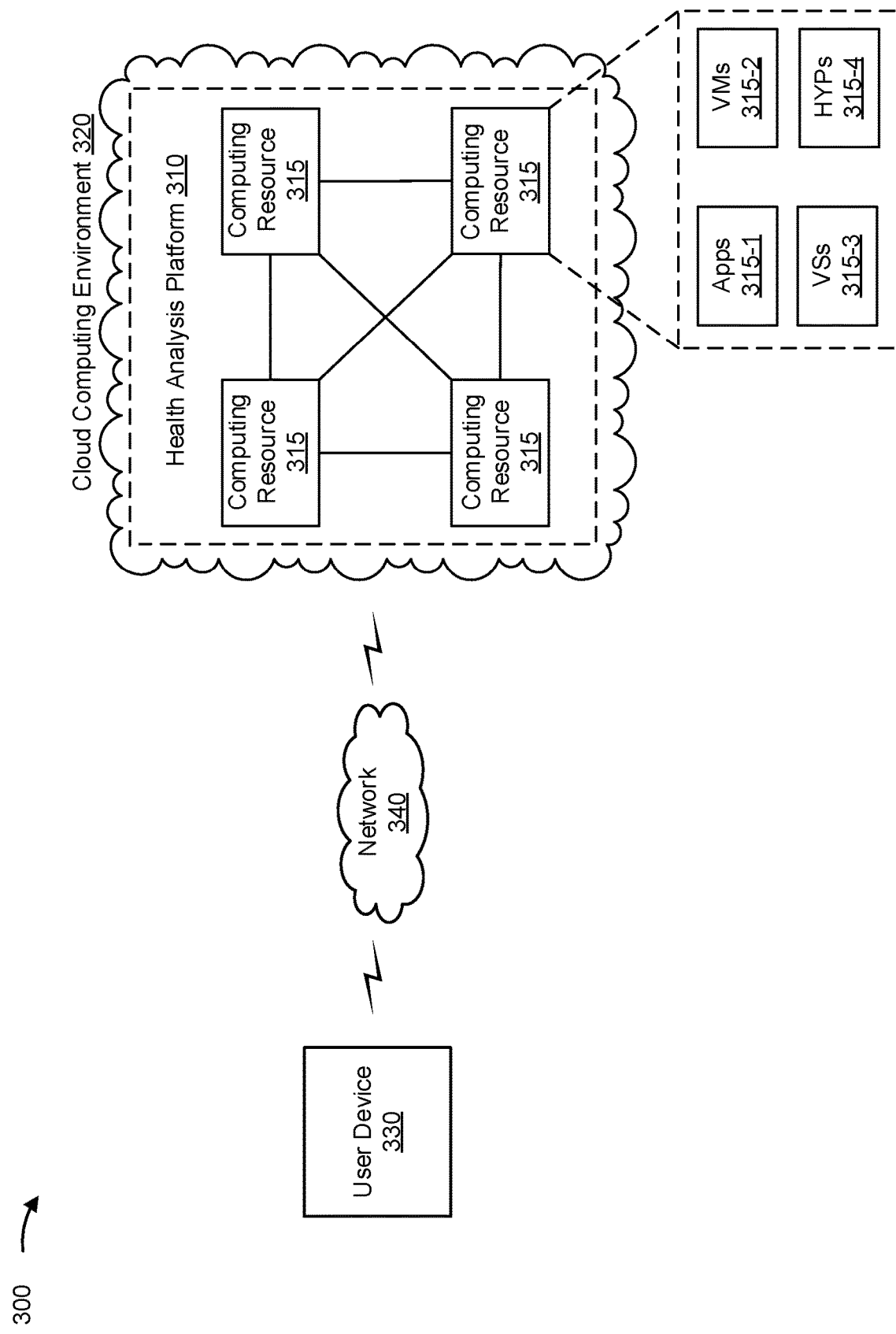
FIG. 3 is a diagram of an example environment in which systems and/or methods described herein may be implemented.

FIG. 3 is a diagram of an example environment 300 in which systems and/or methods described herein may be implemented. As shown in FIG. 3, environment 300 may include a health analysis platform 310, a computing resource 315, a cloud computing environment 320, a user device 330, and a network 340. Devices of environment 300 may interconnect via wired connections, wireless connections, or a combination of wired and wireless connections.

Health analysis platform 310 includes one or more computing resources assigned to determine whether a patient has a particular health condition and/or a likelihood that the patient has the particular health condition. For example, health analysis platform 310 may be a platform implemented by cloud computing environment 320 that may analyze video and/or image data from user device 330, identify physiological activity of a patient, and determine, from the physiological activity, whether the patient is experiencing a stroke, has an inner ear impairment, and/or the like (e.g., based on a signature associated with the physiological activity). In some implementations, health analysis platform 310 is implemented by computing resources 315 of cloud computing environment 320.

Health analysis platform 310 may include a server device or a group of server devices. In some implementations, health analysis platform 310 may be hosted in cloud computing environment 320. Notably, while implementations described herein may describe health analysis platform 310 as being hosted in cloud computing environment 320, in some implementations, health analysis platform 310 may be non-cloud-based or may be partially cloud-based.

Cloud computing environment 320 includes an environment that delivers computing as a service, whereby shared resources, services, and/or the like may be provided to receive, process, generate, and/or provide information associated with detecting stroke or inner ear impairment based on images of physiological activity of a patient. Cloud computing environment 320 may provide computation, software, data access, storage, and/or other services that do not require end-user knowledge of a physical location and configuration of a system and/or a device that delivers the services. As shown, cloud computing environment 320 may include health analysis platform 310 and a computing resource 315.

Computing resource 315 includes one or more personal computers, workstation computers, server devices, or another type of computation and/or communication device. In some implementations, computing resource 315 may host health analysis platform 310. The cloud resources may include compute instances executing in computing resource 315, storage devices provided in computing resource 315, data transfer devices provided by computing resource 315, and/or the like. In some implementations, computing resource 315 may communicate with other computing resources 315 via wired connections, wireless connections, or a combination of wired and wireless connections.

As further shown in FIG. 3, computing resource 315 may include a group of cloud resources, such as one or more applications ("APPs") 315-1, one or more virtual machines ("VMs") 315-2, virtualized storage ("VSs") 315-3, one or more hypervisors ("HYPs") 315-4, or the like.

Application 315-1 includes one or more software applications that may be provided to or accessed by user device 330. Application 315-1 may eliminate a need to install and execute the software applications on user device 330. For example, application 315-1 may include software associated with health analysis platform 310 and/or any other software capable of being provided via cloud computing environment 320. In some implementations, one application 315-1 may send/receive information to/from one or more other applications 315-1, via virtual machine 315-2.

Virtual machine 315-2 includes a software implementation of a machine (e.g., a computer) that executes programs like a physical machine. Virtual machine 315-2 may be either a system virtual machine or a process virtual machine, depending upon use and degree of correspondence to any real machine by virtual machine 315-2. A system virtual machine may provide a complete system platform that supports execution of a complete operating system ("OS"). A process virtual machine may execute a single program and may support a single process. In some implementations, virtual machine 315-2 may execute on behalf of a user (e.g., user device 330), and may manage infrastructure of cloud computing environment 320, such as data management, synchronization, or long-duration data transfers.

Virtualized storage 315-3 includes one or more storage systems and/or one or more devices that use virtualization techniques within the storage systems or devices of computing resource 315. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 315-4 provides hardware virtualization techniques that allow multiple operating systems (e.g., "guest operating systems") to execute concurrently on a host computer, such as computing resource 315. Hypervisor 315-4 may present a virtual operating platform to the guest operating systems and may manage the execution of the guest operating systems. Multiple instances of a variety of operating systems may share virtualized hardware resources.

User device 330 includes one or more devices capable of receiving, generating, storing, processing, and/or providing information associated with detecting stroke or inner ear impairment based on images of physiological activity of a patient. For example, user device 330 may include a communication and/or computing device, such as a mobile phone (e.g., a smart phone, a radiotelephone, etc.), a laptop computer, a tablet computer, a handheld computer, a desktop computer, a gaming device, a wearable communication device (e.g., a smart wristwatch, a pair of smart eyeglasses, etc.), or a similar type of device.

Network 340 includes one or more wired and/or wireless networks. For example, network 340 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 3 are provided as one or more examples. In practice, there may be additional devices and/or networks, fewer devices and/or networks, different devices and/or networks, or differently arranged devices and/or networks than those shown in FIG. 3. Furthermore, two or more devices shown in FIG. 3 may be implemented within a single device, or a single device shown in FIG. 3 may be implemented as multiple, distributed devices. Additionally, or alternatively, a set of devices (e.g., one or more devices) of environment 300 may perform one or more functions described as being performed by another set of devices of environment 300.

Figure 4:
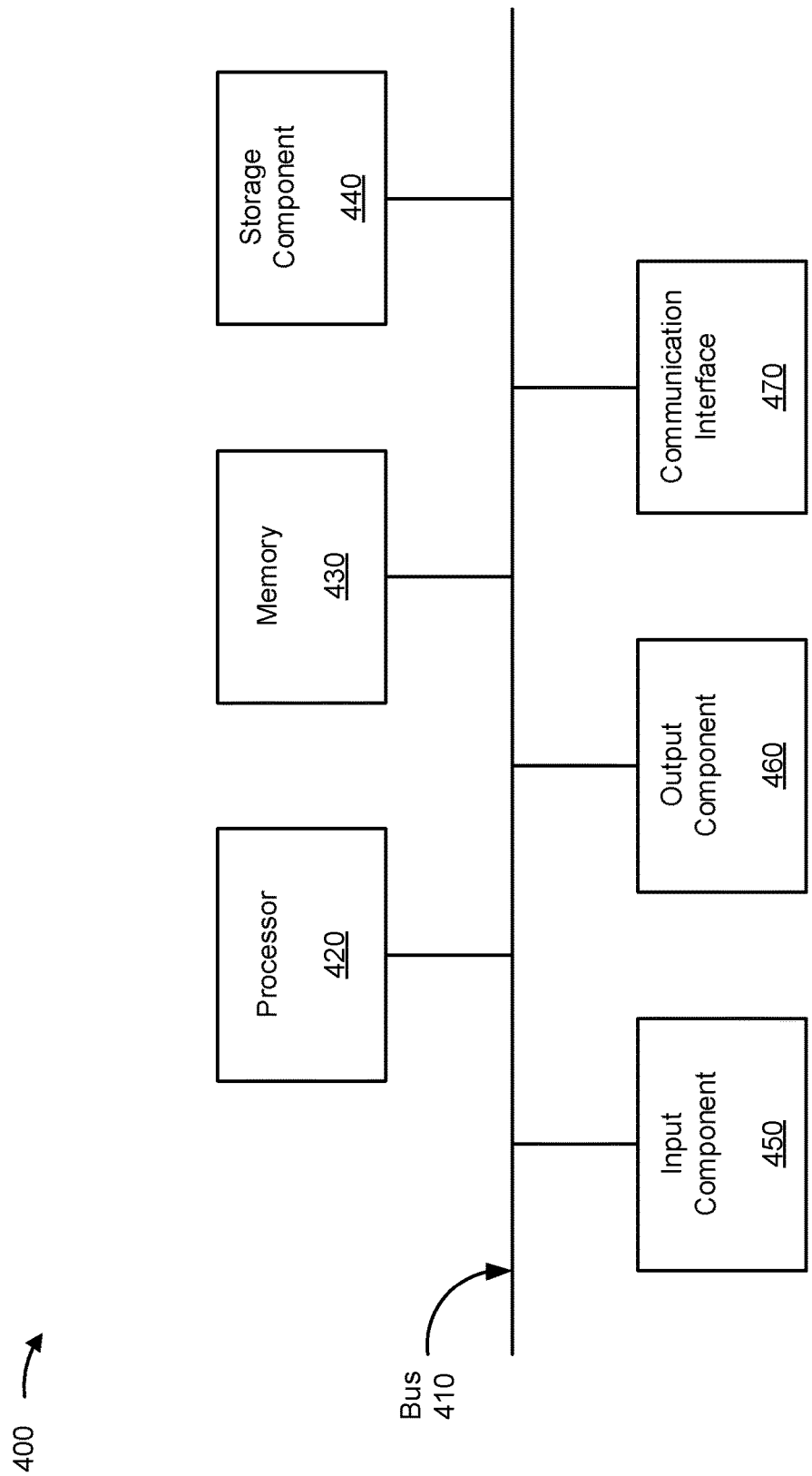
FIG. 4 is a diagram of example components of one or more devices of FIG. 3.

FIG. 4 is a diagram of example components of a device 400. Device 400 may correspond to health analysis platform 310, computing resource 315, and/or user device 330. In some implementations, health analysis platform 310, computing resource 315, and/or user device 330 may include one or more devices 400 and/or one or more components of device 400. As shown in FIG. 4, device 400 may include a bus 410, a processor 420, a memory 430, a storage component 440, an input component 450, an output component 460, and a communication interface 470.

Bus 410 includes a component that permits communication among multiple components of device 400. Processor 420 is implemented in hardware, firmware, and/or a combination of hardware and software. Processor 420 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 420 includes one or more processors capable of being programmed to perform a function. Memory 430 includes a random-access memory (RAM), a read only memory (ROM), and/or another type of dynamic or static storage device (e.g., a flash memory, a magnetic memory, and/or an optical memory) that stores information and/or instructions for use by processor 420.

Storage component 440 stores information and/or software related to the operation and use of device 400. For example, storage component 440 may include a hard disk (e.g., a magnetic disk, an optical disk, and/or a magneto-optic disk), a solid-state drive (SSD), a compact disc (CD), a digital versatile disc (DVD), a floppy disk, a cartridge, a magnetic tape, and/or another type of non-transitory computer-readable medium, along with a corresponding drive.

Input component 450 includes a component that permits device 400 to receive information, such as via user input (e.g., a touch screen display, a keyboard, a keypad, a mouse, a button, a switch, and/or a microphone). Additionally, or alternatively, input component 450 may include a component for determining location (e.g., a global positioning system (GPS) component) and/or a sensor (e.g., an accelerometer, a gyroscope, an actuator, another type of positional or environmental sensor, and/or the like). Output component 460 includes a component that provides output information from device 400 (via, e.g., a display, a speaker, a haptic feedback component, an audio or visual indicator, and/or the like).

Communication interface 470 includes a transceiver-like component (e.g., a transceiver, a separate receiver, a separate transmitter, and/or the like) that enables device 400 to communicate with other devices, such as via a wired connection, a wireless connection, or a combination of wired and wireless connections. Communication interface 470 may permit device 400 to receive information from another device and/or provide information to another device. For example, communication interface 470 may include an Ethernet interface, an optical interface, a coaxial interface, an infrared interface, a radio frequency (RF) interface, a universal serial bus (USB) interface, a Wi-Fi interface, a cellular network interface, and/or the like.

Device 400 may perform one or more processes described herein. Device 400 may perform these processes based on processor 420 executing software instructions stored by a non-transitory computer-readable medium, such as memory 430 and/or storage component 440. As used herein, the term "computer-readable medium" refers to a non-transitory memory device. A memory device includes memory space within a single physical storage device or memory space spread across multiple physical storage devices.

Software instructions may be read into memory 430 and/or storage component 440 from another computer-readable medium or from another device via communication interface 470. When executed, software instructions stored in memory 430 and/or storage component 440 may cause processor 420 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 4 are provided as an example. In practice, device 400 may include additional components, fewer components, different components, or differently arranged components than those shown in FIG. 4. Additionally, or alternatively, a set of components (e.g., one or more components) of device 400 may perform one or more functions described as being performed by another set of components of device 400.

Figure 5:
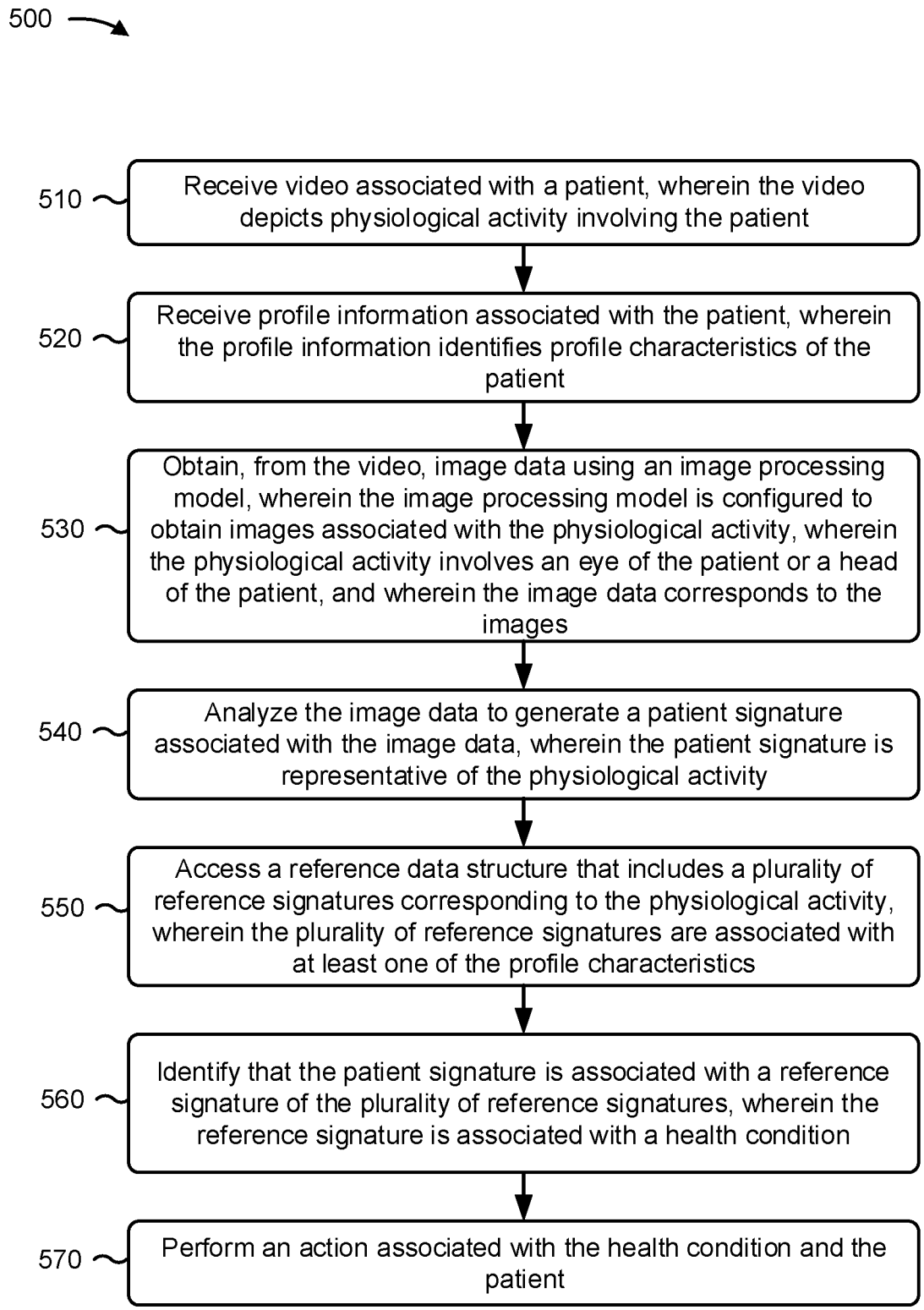
FIGS. 5-7 are flow charts of example processes for detecting stroke or inner ear impairment based on images of physiological activity of a patient.

FIG. 5 is a flow chart of an example process 500 for detecting stroke or inner ear impairment based on images of physiological activity of a patient. In some implementations, one or more process blocks of FIG. 5 may be performed by health analysis platform (e.g., health analysis platform 310). In some implementations, one or more process blocks of FIG. 5 may be performed by another device or a group of devices separate from or including the health analysis platform, such as a user device (e.g., user device 330) and/or other type of device or system.

As shown in FIG. 5, process 500 may include receiving a video associated with a patient, wherein the video depicts physiological activity involving the patient (block 510). For example, the health analysis platform (e.g., using processor 420, memory 430, storage component 440, input component 450, output component 460, communication interface 470 and/or the like) may receive a video associated with a patient, as described above. In some implementations, the video depicts physiological activity involving the patient.

As further shown in FIG. 5, process 500 may include receiving profile information associated with the patient, wherein the profile information identifies profile characteristics of the patient (block 520). For example, the health analysis platform (e.g., using processor 420, memory 430, storage component 440, input component 450, output component 460, communication interface 470 and/or the like) may receive profile information associated with the patient, as described above. In some implementations, the profile information identifies profile characteristics of the patient.

As further shown in FIG. 5, process 500 may include obtaining, from the video, image data using an image processing model, wherein the image processing model is configured to obtain images associated with the physiological activity, wherein the physiological activity involves an eye of the patient or a head of the patient, and wherein the image data corresponds to the images (block 530). For example, the health analysis platform (e.g., using processor 420, memory 430, storage component 440, input component 450, output component 460, communication interface 470 and/or the like) may obtain, from the video, image data using an image processing model, as described above. In some implementations, the image processing model is configured to obtain images associated with the physiological activity. In some implementations, the physiological activity involves an eye of the patient or a head of the patient. In some implementations, the image data corresponds to the images.

As further shown in FIG. 5, process 500 may include analyzing the image data to generate a patient signature associated with the image data, wherein the patient signature is representative of the physiological activity (block 540). For example, the health analysis platform (e.g., using processor 420, memory 430, storage component 440, input component 450, output component 460, communication interface 470 and/or the like) may analyze the image data to generate a patient signature associated with the image data, as described above. In some implementations, the patient signature is representative of the physiological activity.

As further shown in FIG. 5, process 500 may include accessing a reference data structure that includes a plurality of reference signatures corresponding to the physiological activity, wherein the plurality of reference signatures are associated with at least one of the profile characteristics (block 550). For example, the health analysis platform (e.g., using processor 420, memory 430, storage component 440, input component 450, output component 460, communication interface 470 and/or the like) may access a reference data structure that includes a plurality of reference signatures corresponding to the physiological activity, as described above. In some implementations, the plurality of reference signatures are associated with at least one of the profile characteristics.

As further shown in FIG. 5, process 500 may include identifying that the patient signature is associated with a reference signature of the plurality of reference signatures, wherein the reference signature is associated with a health condition (block 560). For example, the health analysis platform (e.g., using processor 420, memory 430, storage component 440, input component 450, output component 460, communication interface 470 and/or the like) may identify that the patient signature is associated with a reference signature of the plurality of reference signatures, as described above. In some implementations, the reference signature is associated with a health condition.

As further shown in FIG. 5, process 500 may include performing an action associated with the health condition and the patient (block 570). For example, the health analysis platform (e.g., using processor 420, memory 430, storage component 440, input component 450, output component 460, communication interface 470 and/or the like) may perform an action associated with the health condition and the patient, as described above.

Process 500 may include additional implementations, such as any single implementation or any combination of implementations described below and/or in connection with one or more other processes described elsewhere herein.

In a first implementation, the user device includes a camera that provides the video of the physiological activity. In a second implementation, alone or in combination with the first implementation, the profile information associated with the patient is received via a user interface associated with an application of the user device, and the user interface is configured to prompt a user of the user device for the profile information.

In a third implementation, alone or in combination with one or more of the first and second implementations, the image processing model comprises at least one of: a facial recognition model or a gaze detection model.

In a fourth implementation, alone or in combination with one or more of the first through third implementations, the patient signature is generated based on translating, according to a signature model, image coordinates of features of the eye or the head to data points for the patient signature, and the signature model is used to generate the patient signature and the plurality of reference signatures.

In a fifth implementation, alone or in combination with one or more of the first through fourth implementations, the reference signature is a first reference signature and the health condition is a first health condition, and the health analysis platform may identify that the patient signature may be associated with a second reference signature wherein the second reference signature is associated with a second health condition; determine, based on the physiological activity, a first probability that the patient has the first health condition based on the patient signature and the first reference signature, determine, based on the physiological activity, a second probability that the patient has a second health condition based on the patient signature and the second reference signature, and when, performing the action, the health analysis platform may cause a user interface to present information identifying the first probability that the patient has the first health condition and the second probability that the patient has the second health condition.

In a sixth implementation, alone or in combination with one or more of the first through fifth implementations, the health analysis platform may store the patient signature in the reference data structure to train a machine learning model associated with diagnosing the health condition.

In a seventh implementation, alone or in combination with one or more of the first through sixth implementations, the health analysis platform, when performing the action, may transmit a communication to a user device to notify an entity of the user device that the patient may have the health condition. In an eighth implementation, alone or in combination with one or more of the first through seventh implementations, the health analysis platform, when performing the action, may cause a display to present at least one of: information identifying that the patient may have the health condition, a treatment plan associated with the health condition, or contact information associated with a healthcare provider that can treat the health condition.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
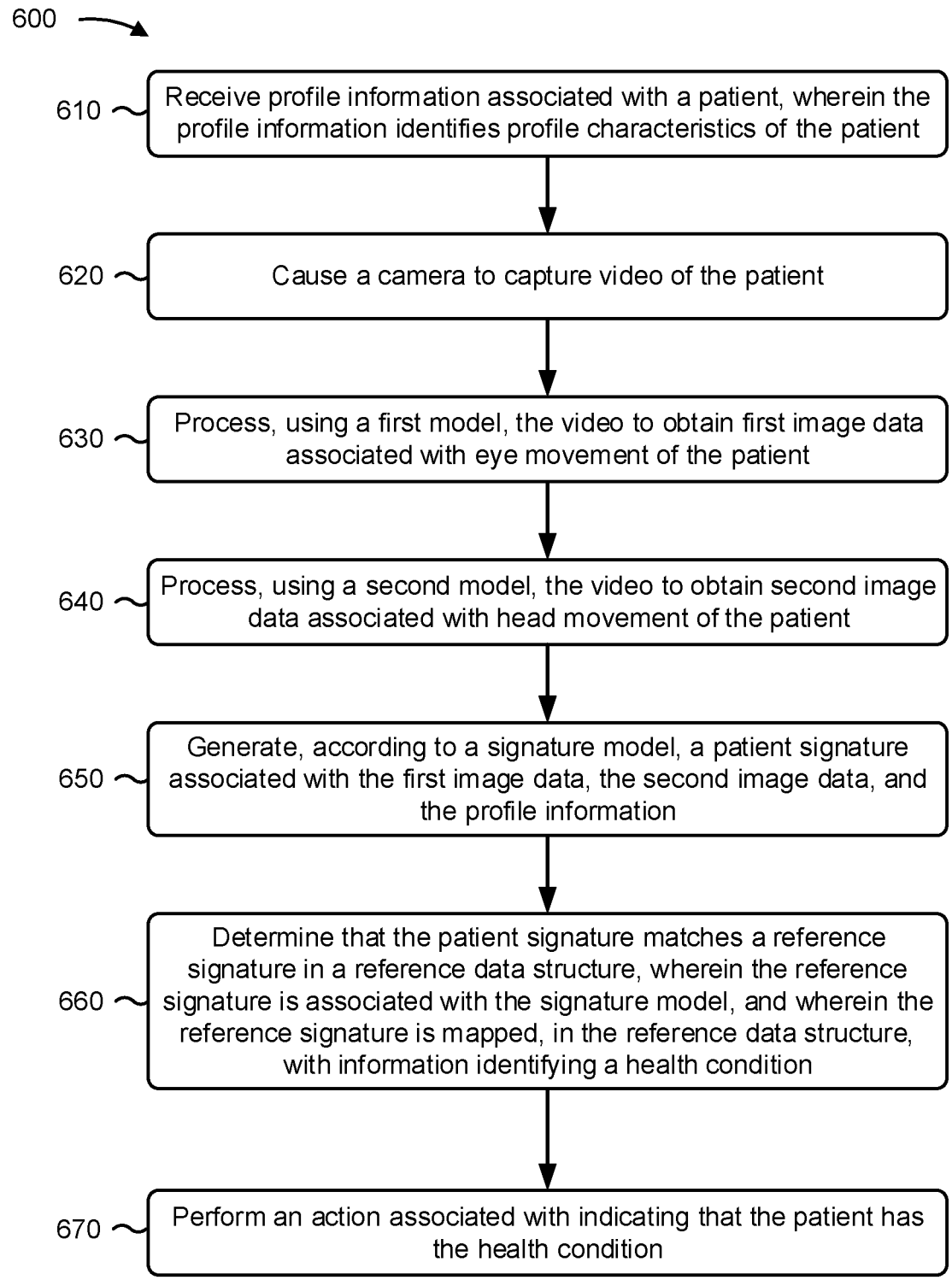

FIG. 6 is a flow chart of an example process 600 for detecting stroke or inner ear impairment based on images of physiological activity of a patient. In some implementations, one or more process blocks of FIG. 6 may be performed by health analysis platform (e.g., health analysis platform 310). In some implementations, one or more process blocks of FIG. 6 may be performed by another device or a group of devices separate from or including the health analysis platform, such as a user device (e.g., user device 330) and/or other type of device or system.

As shown in FIG. 6, process 600 may include receiving profile information associated with a patient, wherein the profile information identifies profile characteristics of the patient (block 610). For example, the health analysis platform (e.g., using processor 420, memory 430, storage component 440, input component 450, output component 460, communication interface 470 and/or the like) may receive profile information associated with a patient, as described above. In some implementations, the profile information identifies profile characteristics of the patient.

As further shown in FIG. 6, process 600 may include causing a camera to capture video of the patient (block 620). For example, the health analysis platform (e.g., using processor 420, memory 430, storage component 440, input component 450, output component 460, communication interface 470 and/or the like) may cause a camera to capture video of the patient, as described above.

As further shown in FIG. 6, process 600 may include processing, using a first model, the video to obtain first image data associated with eye movement of the patient (block 630). For example, the health analysis platform (e.g., using processor 420, memory 430, storage component 440, input component 450, output component 460, communication interface 470 and/or the like) may process, using a first model, the video to obtain first image data associated with eye movement of the patient, as described above.

As further shown in FIG. 6, process 600 may include processing, using a second model, the video to obtain second image data associated with head movement of the patient (block 640). For example, the health analysis platform (e.g., using processor 420, memory 430, storage component 440, input component 450, output component 460, communication interface 470 and/or the like) may process, using a second model, the video to obtain second image data associated with head movement of the patient, as described above.

As further shown in FIG. 6, process 600 may include generating, according to a signature model, a patient signature associated with the first image data, the second image data, and the profile information (block 650). For example, the health analysis platform (e.g., using processor 420, memory 430, storage component 440, input component 450, output component 460, communication interface 470 and/or the like) may generate, according to a signature model, a patient signature associated with the first image data, the second image data, and the profile information, as described above.

As further shown in FIG. 6, process 600 may include determining that the patient signature matches a reference signature in a reference data structure, wherein the reference signature is associated with the signature model and wherein the reference signature is mapped, in the reference data structure, with information identifying a health condition (block 660). For example, the health analysis platform (e.g., using processor 420, memory 430, storage component 440, input component 450, output component 460, communication interface 470 and/or the like) may determine that the patient signature matches a reference signature in a reference data structure, as described above. In some implementations, the reference signature is associated with the signature model. In some implementations, the reference signature is mapped, in the reference data structure, with information identifying a health condition.

As further shown in FIG. 6, process 600 may include performing an action associated with indicating that the patient has the health condition (block 670). For example, the health analysis platform (e.g., using processor 420, memory 430, storage component 440, input component 450, output component 460, communication interface 470 and/or the like) may perform an action associated with indicating that the patient has the health condition, as described above.

Process 600 may include additional implementations, such as any single implementation or any combination of implementations described below and/or in connection with one or more other processes described elsewhere herein.

In a first implementation, the first model is associated with a gaze detection model, and the second model is associated with a facial recognition model. In a second implementation, alone or in combination with the first implementation, the signature model enables generation of the patient signature by translating coordinates of features of one of more eyes of the patient to generate first data points of the patient signature, translating coordinates of features of a head of the patient to generate second data points of the patient signature, and combining the first data points, the second data points, and the profile information to generate the patient signature. In a third implementation, alone or in combination with one or more of the first and second implementations, the camera is in communication with the user device, and the camera is controlled via a user interface of an application installed on the user device.

In a fourth implementation, alone or in combination with one or more of the first through third implementations, the patient signature is determined to match the reference signature based on a threshold percentage of data points of the patient signature matching the reference signature. In a fifth implementation, alone or in combination with one or more of the first through fourth implementations, the health condition indicates whether urgent medical attention should be given to the patient.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7:
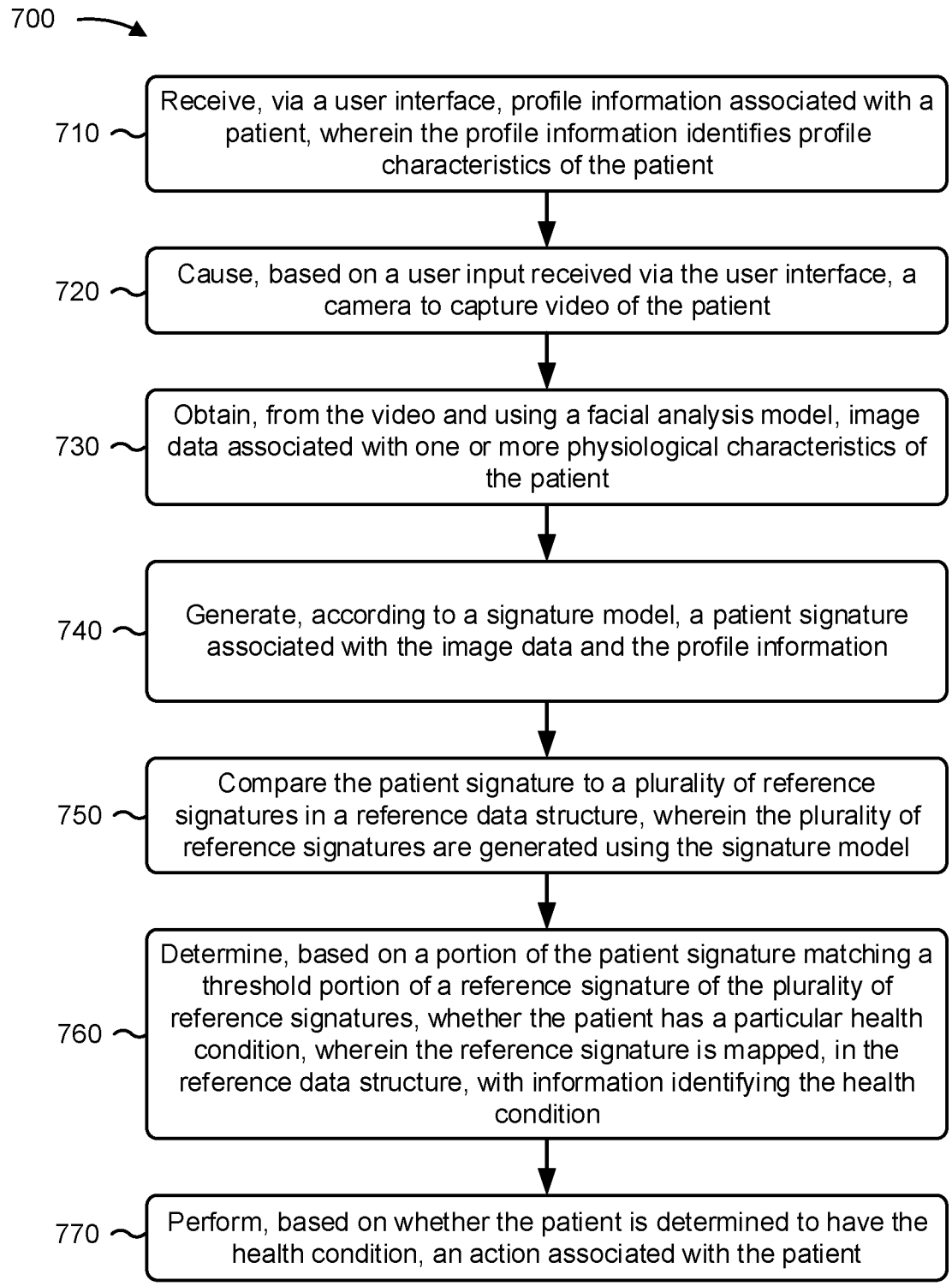

FIG. 7 is a flow chart of an example process 700 for detecting stroke or inner ear impairment based on images of physiological activity of a patient. In some implementations, one or more process blocks of FIG. 7 may be performed by health analysis platform (e.g., health analysis platform 310). In some implementations, one or more process blocks of FIG. 7 may be performed by another device or a group of devices separate from or including the health analysis platform, such as a user device (e.g., user device 330) and/or other type of device or system.

As shown in FIG. 7, process 700 may include receiving, via a user interface, profile information associated with a patient, wherein the profile information identifies profile characteristics of the patient (block 710). For example, the health analysis platform (e.g., using processor 420, memory 430, storage component 440, input component 450, output component 460, communication interface 470 and/or the like) may receive, via a user interface, profile information associated with a patient, as described above. In some implementations, the profile information identifies profile characteristics of the patient.

As further shown in FIG. 7, process 700 may include causing, based on a user input received via the user interface, a camera to capture video of the patient (block 720). For example, the health analysis platform (e.g., using processor 420, memory 430, storage component 440, input component 450, output component 460, communication interface 470 and/or the like) may cause, based on a user input received via the user interface, a camera to capture video of the patient, as described above.

As further shown in FIG. 7, process 700 may include obtaining, from the video and using a facial analysis model, image data associated with one or more physiological characteristics of the patient (block 730). For example, the health analysis platform (e.g., using processor 420, memory 430, storage component 440, input component 450, output component 460, communication interface 470 and/or the like) may obtain, from the video and using a facial analysis model, image data associated with one or more physiological characteristics of the patient, as described above.

As further shown in FIG. 7, process 700 may include generating, according to a signature model, a patient signature associated with the image data and the profile information (block 740). For example, the health analysis platform (e.g., using processor 420, memory 430, storage component 440, input component 450, output component 460, communication interface 470 and/or the like) may generate, according to a signature model, a patient signature associated with the image data and the profile information, as described above.

As further shown in FIG. 7, process 700 may include comparing the patient signature to a plurality of reference signatures in a reference data structure, wherein the plurality of reference signatures are generated using the signature model (block 750). For example, the health analysis platform (e.g., using processor 420, memory 430, storage component 440, input component 450, output component 460, communication interface 470 and/or the like) may compare the patient signature to a plurality of reference signatures in a reference data structure, as described above. In some implementations, the plurality of reference signatures are generated using the signature model.

As further shown in FIG. 7, process 700 may include determining, based on a portion of the patient signature matching a threshold portion of a reference signature of the plurality of reference signatures, whether the patient has a particular health condition, wherein the reference signature is mapped, in the reference data structure, with information identifying the health condition (block 760). For example, the health analysis platform (e.g., using processor 420, memory 430, storage component 440, input component 450, output component 460, communication interface 470 and/or the like) may determine, based on a portion of the patient signature matching a threshold portion of a reference signature of the plurality of reference signatures, whether the patient has a particular health condition, as described above. In some implementations, the reference signature is mapped, in the reference data structure, with information identifying the health condition.

As further shown in FIG. 7, process 700 may include performing, based on whether the patient has the health condition, an action associated with the patient (block 770). For example, the health analysis platform (e.g., using processor 420, memory 430, storage component 440, input component 450, output component 460, communication interface 470 and/or the like) may perform, based on whether the patient has the health condition, an action associated with the patient, as described above.

Process 700 may include additional implementations, such as any single implementation or any combination of implementations described below and/or in connection with one or more other processes described elsewhere herein.

In a first implementation, the one or more physiological characteristics comprise at least one of movement of an eye of the patient, movement of a pupil or iris of the patient, position of an eye of the patient, movement of a head of the patient, position of a head of the patient, movement of a skeletal structure of the patient, or position of a skeletal structure of the patient.

In a second implementation, alone or in combination with the first implementation, the image data is associated with images of an eye of the patient or a head of the patient, and the patient signature is representative of eye movement or head movement of the patient.

In a third implementation, alone or in combination with one or more of the first and second implementations, at least two of the plurality of reference signatures are associated with the health condition being related to a stroke or the health condition being related to having an inner ear impairment.

In a fourth implementation, alone or in combination with one or more of the first through third implementations, the health analysis platform may cause the user interface to display whether the patient has the health condition, cause, when the patient is determined to have the health condition, the user interface to display information associated with treating the health condition, or transmit, when the patient is determined to have the health condition, a message that identifies the health condition and the profile information of the patient.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

The foregoing disclosure provides illustration and description but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   receiving, by a user device, video associated with a patient,
      wherein the video depicts physiological activity involving the patient;
   receiving, by the user device, profile information associated with the patient,
   wherein the profile information identifies profile characteristics of the patient;
   obtaining, by the user device and from the video, image data using an image processing model,
      wherein the image processing model is configured to obtain images associated with the physiological activity,
      wherein the physiological activity involves an eye of the patient or a head of the patient, and
      wherein the image data corresponds to the images;
   analyzing, by the user device, the image data to generate a patient signature associated with the image data,
      wherein the patient signature is representative of the physiological activity;
   accessing, by the user device, a reference data structure that includes a plurality of reference signatures corresponding to the physiological activity, wherein the plurality of reference signatures are associated with at least one of the profile characteristics;
identifying, by the user device, that the patient signature is associated with a reference signature of the plurality of reference signatures,
wherein the reference signature is associated with a health condition; and
performing, by the user device, an action associated with the health condition and the patient.

2. The method of claim 1, wherein the user device includes a camera that provides the video of the physiological activity.

3. The method of claim 1, wherein the profile information associated with the patient is received via a user interface associated with an application of the user device,
wherein the user interface is configured to prompt a user of the user device for the profile information.

4. The method of claim 1, wherein the image processing model comprises at least one of:
a facial recognition model, or
a gaze detection model.

5. The method of claim 1, wherein the patient signature is generated based on translating, according to a signature model, image coordinates of features of the eye or the head to data points for the patient signature,
wherein the signature model is used to generate the patient signature and the plurality of reference signatures.

6. The method of claim 1, wherein the reference signature is a first reference signature and the health condition is a first health condition, the method further comprising:
identifying that the patient signature may be associated with a second reference signature,
wherein the second reference signature is associated with a second health condition;
determining, based on the physiological activity, a first probability that the patient has the first health condition based on the patient signature and the first reference signature; and
determining, based on the physiological activity, a second probability that the patient has a second health condition based on the patient signature and the second reference signature,
wherein performing the action comprises:
causing a user interface to present information identifying the first probability that the patient has the first health condition and the second probability that the patient has the second health condition.

7. The method of claim 1, further comprising:
storing the patient signature in the reference data structure to train a machine learning model associated with diagnosing the health condition.

8. The method of claim 1, wherein performing the action comprises transmitting a communication to a user device to notify an entity of the user device that the patient may have the health condition.

9. The method of claim 1, wherein performing the action comprises causing a display to present at least one of:
information identifying that the patient may have the health condition,
a treatment plan associated with the health condition, or
contact information associated with a healthcare provider that can treat the health condition.

10. A user device, comprising:
one or more memories; and
one or more processors, communicatively coupled to the one or more memories, to:
receive profile information associated with a patient,
wherein the profile information identifies profile characteristics of the patient;
cause a camera to capture video of the patient;
process, using a first model, the video to obtain first image data associated with eye movement of the patient;
process, using a second model, the video to obtain second image data associated with head movement of the patient;
generate, according to a signature model, a patient signature associated with the first image data, the second image data, and the profile information;
determine that the patient signature matches a reference signature in a reference data structure,
wherein the reference signature is associated with the signature model, and
wherein the reference signature is mapped, in the reference data structure, with information identifying a health condition; and
perform an action associated with indicating that the patient has the health condition.

11. The user device of claim 10, wherein the first model is associated with a gaze detection model, and
wherein the second model is associated with a facial recognition model.

12. The user device of claim 10, wherein the signature model enables generation of the patient signature by:
translating coordinates of features of one of more eyes of the patient to generate first data points of the patient signature,
translating coordinates of features of a head of the patient to generate second data points of the patient signature, and
combining the first data points, the second data points, and the profile information to generate the patient signature.

13. The user device of claim 10, wherein the camera is in communication with the user device, and
wherein the camera is controlled via a user interface of an application installed on the user device.

14. The user device of claim 10, wherein the patient signature is determined to match the reference signature based on a threshold percentage of data points of the patient signature matching the reference signature.

15. The user device of claim 10, wherein the health condition indicates whether urgent medical attention should be given to the patient.

16. A non-transitory computer-readable medium storing instructions, the instructions comprising:
one or more instructions that, when executed by one or more processors of a user device, cause the one or more processors to:
receive, via a user interface, profile information associated with a patient,
wherein the profile information identifies profile characteristics of the patient;
cause, based on a user input received via the user interface, a camera to capture video of the patient;
obtain, from the video and using a facial analysis model, image data associated with one or more physiological characteristics of the patient;
generate, according to a signature model, a patient signature associated with the image data and the profile information;
compare the patient signature to a plurality of reference signatures in a reference data structure, wherein the plurality of reference signatures are generated using the signature model;

determine, based on a portion of the patient signature matching a threshold portion of a reference signature of the plurality of reference signatures, that the patient has a particular health condition, wherein the reference signature is mapped, in the reference data structure, with information identifying the health condition; and perform, based on determining that the patient has the health condition, an action associated with the patient.

17. The non-transitory computer-readable medium of claim 16, wherein the one or more physiological characteristics comprise at least one of:

movement of an eye of the patient,
movement of a pupil or iris of the patient,
position of an eye of the patient,
movement of a head of the patient,
position of a head of the patient,
movement of a skeletal structure of the patient, or
position of a skeletal structure of the patient.

18. The non-transitory computer-readable medium of claim 16, wherein the image data is associated with images of an eye of the patient or a head of the patient, and wherein the patient signature is representative of eye movement or head movement of the patient.

19. The non-transitory computer-readable medium of claim 16, wherein at least two of the plurality of reference signatures are associated with the health condition being related to a stroke or the health condition being related to having an inner ear impairment.

20. The non-transitory computer-readable medium of claim 16, wherein the one or more instructions, that cause the one or more processors to perform the action, cause the one or more processors to:

cause the user interface to display whether the patient has the health condition, cause, when the patient is determined to have the health condition, the user interface to display information associated with treating the health condition, or transmit, when the patient is determined to have the health condition, a message that identifies the health condition and the profile information of the patient, wherein the message is transmitted, via a communication device of the user device, to an entity associated with providing medical treatment.

\* \* \* \* \*